United States Patent
Magnone et al.

(10) Patent No.: US 11,207,360 B2
(45) Date of Patent: Dec. 28, 2021

(54) COMPOSITION FOR THE TREATMENT OF DYSBIOSIS OF THE INTESTINAL MICROBIOTA

(71) Applicant: NUTRAVIS S.R.L., Genoa (IT)

(72) Inventors: Mirko Magnone, Genoa (IT); Elena Zocchi, Genoa (IT)

(73) Assignee: NUTRAVIS S.R.L., Genoa (IT)

( * ) Notice: Subject to any disclaimer, the term of this patent is extended or adjusted under 35 U.S.C. 154(b) by 0 days.

(21) Appl. No.: 16/763,114

(22) PCT Filed: Nov. 26, 2018

(86) PCT No.: PCT/IB2018/059303
§ 371 (c)(1),
(2) Date: May 11, 2020

(87) PCT Pub. No.: WO2019/106518
PCT Pub. Date: Jun. 6, 2019

(65) Prior Publication Data
US 2020/0376048 A1 Dec. 3, 2020

(30) Foreign Application Priority Data
Nov. 28, 2017 (IT) .................. 102017000136781

(51) Int. Cl.
| | | |
|---|---|---|
| *A61K 35/747* | (2015.01) | |
| *A61P 3/04* | (2006.01) | |
| *A61P 3/06* | (2006.01) | |
| *A61P 3/10* | (2006.01) | |
| *A61K 31/015* | (2006.01) | |
| *A61K 35/742* | (2015.01) | |
| *A61K 35/745* | (2015.01) | |
| *A61K 31/047* | (2006.01) | |
| *A61K 31/122* | (2006.01) | |
| *A61K 31/336* | (2006.01) | |

(52) U.S. Cl.
CPC .......... *A61K 35/747* (2013.01); *A61K 31/015* (2013.01); *A61K 35/742* (2013.01); *A61K 35/745* (2013.01); *A61P 3/04* (2018.01); *A61P 3/06* (2018.01); *A61P 3/10* (2018.01); *A61K 31/047* (2013.01); *A61K 31/122* (2013.01); *A61K 31/336* (2013.01)

(58) Field of Classification Search
None
See application file for complete search history.

(56) References Cited

U.S. PATENT DOCUMENTS

| | | | |
|---|---|---|---|
| 10,688,139 B2* | 6/2020 | Breton | A61K 35/747 |
| 2007/0082044 A1 | 4/2007 | Yeum | |
| 2007/0178078 A1* | 8/2007 | Khoo | A23K 10/18 424/93.45 |
| 2012/0039852 A1* | 2/2012 | Darimont-Nicolau | A61K 31/715 424/93.3 |
| 2013/0316041 A1* | 11/2013 | Maranz | A23L 33/135 426/2 |
| 2017/0028000 A1 | 2/2017 | Grompone et al. | |

FOREIGN PATENT DOCUMENTS

| | | |
|---|---|---|
| EP | 2216036 A1 | 8/2010 |
| IN | 2013 CH00653 | * 10/2014 |

OTHER PUBLICATIONS

Onning, G. Influence of a Drink Containing Different Antioxidants and Lactobacillus plantarum 299v . . . Int J of Food Sciences & Nutrition 54(4)281-289, Jul. 2003. (Year: 2003).*

Bassaganya-Riera J. et al, "Abscisic acid regulates inflammation via ligand-binding domain-independent activation of peroxisome proliferator-activated receptor?", Journal of Biological Chemistry, vol. 286, No. 4, Jan. 28, 2011, pp. 2504-2516.

Guri A.J. et al., "Abscisic acid ameliorates experimental IBD by downregulating cellular adhesion molecules expression and suppressing immune cell infiltration", Clinical Nutrition, vol. 29, No. 6, Dec. 1, 2010, pp. 824-831.

Inomata M. et al., "Biosynthesis of abscisic acid by the direct pathway via ionylideneethane in a fungus, *Cercospora cruenta*" Bioscience, Biotechnology, and Biochemistry, Jan. 1, 2004, pp. 2571-2580.

Search Report and Written Opinion of PCT/IB2018/059303 dated Feb. 22, 2019.

Tian-Quiong Shi et al., "Microbial production of plant hormones: opportunities and challenges", Bioengineered, vol. 8, No. 2, Jul. 26, 2016, pp. 124-128.

Viladomiu M. et al., "Nutritional protective mechanisms against gut inflammation", The Journal of Nutritional Biochemistry, vol. 24, No. 6, Mar. 27, 2013, pp. 929-939.

International Preliminary Report on Patentability of PCT/IB2018/059303 dated Nov. 20, 2019.

* cited by examiner

*Primary Examiner* — Ralph J Gitomer
(74) *Attorney, Agent, or Firm* — Silvia Salvadori, P.C.; Silvia Salvadori

(57) ABSTRACT

A pharmaceutical composition comprising at least a probiotic and at least a carotene, for the treatment of dysbiosis of the intestinal microbiota, is disclosed. The association of these ingredients allowed to obtain a clear synergistic effect.

10 Claims, 3 Drawing Sheets

COMPOSITION FOR THE TREATMENT OF DYSBIOSIS OF THE INTESTINAL MICROBIOTA

This application is a U.S. national stage of PCT/IB32018/059303 filed on 26 Nov. 2018, which claims priority to and the benefit of Italian Application No. 102017000136781 filed on 28 Nov. 2017, the contents of which are incorporated herein by reference in their entireties.

FIELD OF THE INVENTION

The present invention concerns a pharmaceutical composition comprising at least a probiotic and at least a carotene, for the treatment of dysbiosis of the intestinal microbiota. the association of these ingredients allowed to obtain a clear synergistic effect.

STATE OF THE ART

The human body contains one log more microbial cells ($\sim 10^{14}$) than human cells. These microorganisms practically colonize every surface of the human body that is exposed to external environment, including the skin, oral cavity, respiratory, urogenital and gastrointestinal tract and all together they constitute the microbiome. Of these body sites, the gastrointestinal (GI) tract is by far the most densely colonized organ. The complex community of microorganisms residing in or passing through the GI tract is referred to as the intestinal microbiota (IM).

The GI tract is a complex and dynamic ecosystem containing a diverse collection of microorganisms. The vast majority of all microbial cells in the human GI tract are bacteria by belonging to, at the phylum-level, two phyla, the *Bacteroidetes* and the *Firmicutes*. Host physiology and intestinal microbiota are intimately connected. This is evident from the fact that each distinct anatomical region along the GI tract is characterized by its own physiochemical conditions, and that these changing conditions exert a selective pressure on the microbiota. The physiochemical conditions that influence the composition of the intestinal microbiota include: intestinal motility, pH, redox potential, nutrient supplies, host secretions (e.g. hydrochloric acid, digestive enzymes, bile and mucus), and the presence of an intact ileocecal valve. Thus, the GI tract harbours many distinct niches, each containing a different microbial ecosystem that varies according to the location within the GI tract. This is already demonstrated by the fact that the microbial density increases along the GI tract. Indeed, per gram of intestinal content, the microbial density increases from $10^1$-$10^4$ microbial cells in the stomach and duodenum, $10^4$-$10^8$ cells in the jejunum and ileum, to $10^{10}$-$10^{12}$ cells in the colon and faeces.

Recently, the collective genome of the human IM (i.e. the human intestinal microbiome) was estimated to contain 3.3 million microbial genes, which is ~150 times more genes than the human genome. The presence of this wide array of genes in addition to our own genome, suggests that a profound influence of intestinal microorganisms on the human body can be expected.

The IM plays an important role in metabolic, nutritional, physiological and immunological processes in the human body. It exerts important metabolic activities by extracting energy from otherwise indigestible dietary polysaccharides such as resistant starch and dietary fibers. These metabolic activities also lead to the production of fundamental nutrients such as short-chain fatty acids (SCFA), vitamins (e.g. vitamin K, vitamin B12 and folic acid) and amino acids, which humans are unable to produce by themselves.

Some of these microbiota-related metabolites such as SCFA and bile acids play pivotal role, for example, in the regulation of host glucose homeostasis. Indeed, microbiota composition and function can integrate the functional states of food intake, affecting whole body energy homeostasis, insulin tolerance and glycaemic response in steady state and during progression of obesity and T2DM.

SCFA including acetate, propionate, and butyrate are widely studied metabolites that are produced by bacterial fermentation of polysaccharides. It has been reported that diet supplementation with SCFA leads to improved glucose tolerance and insulin sensitivity in both lean and obese and diabetic humans. Bile acids are derived from hepatic cholesterol catabolism. Newly synthesized bile acids are conjugated and transported into the gallbladder and postprandial contraction of the gallbladder empties the bile acids into the intestinal lumen. In addition to their role in dietary fat digestion, bile acids are now recognized as important regulators of lipid metabolism, energy homeostasis, glycaemic control, and they can strongly interact with the gut microbiota.

Another important role of the IM is that it is involved in the defence against pathogens through mechanisms such as colonization resistance and production of antimicrobial compounds. In addition, the IM participates in the development, maturation and maintenance of the GI sensory and motoric functions, the intestinal barrier and the mucosal immune system.

The IM and the host have co-evolved. Human evolution has taken place amidst a world of microorganisms. Symbiotic microorganisms have occupied the niches offered by the gastrointestinal tract and probably adapted to the local circumstances. This in turn may have influenced human evolution in terms of metabolic and nutritional requirements. Ultimately, man depends on its IM for a number of vital functions and thus these intestinal microorganisms may contribute to health. Perturbation of the microbiota composition, also known as dysbiosis, has been recognized in various diseases, of which many are associated with the GI tract.

Indeed, a role for the IM in the pathogenesis of several diseases and disorders has been suggested. Multiple studies in the recent years hypothesize that microbiome is critically important for normal host functions, while impaired host microbiome interactions contribute to the pathogenesis of numerous common disorders. Of these, much attention is recently given to the involvement of microbiome in the pathogenesis of impaired glucose tolerance, type 2 diabetes mellitus (T2DM), and other metabolic disorders comprising the metabolic syndrome (MetS), including obesity, non-alcoholic fatty liver disease and their complications.

In particular, several studies suggested an association between compositional and functional microbiome alteration (dysbiosis) and the risk of developing metabolic syndrome-associated pathologies such as obesity and T2DM.

In a study of 292 Danish individuals, has been reported that participants with insulin resistance (as well as increased adiposity) are characterized by a situation of dysbiosis due to higher abundances of *Proteobacteria* and *Bacteroidetes*. Another study described higher abundances of the same phyla in diabetic males as well as a positive correlation between *Bacteroidetes*-to-*Firmicutes* ratio and elevated plasma glucose levels. Moreover, Qin et al. reported in their cohort of 345 Chinese individuals' association between T2DM and higher levels of *E. coli* and *Bacteroidetes*, as well as *Akkermansia muciniphila* and various *Clostridia*.

Not only T2DM seems to be linked with dysbiotic microbiota, but also obesity, a complex disease characterized by excess of body fat accumulation and a well-established risk factor for the onset of hyperglycaemia and insulin resistance, has been associated with phylum-level changes in the composition of IM. Indeed, it has been reported that obese and non-obese subjects have a different gut microbial profile. In particular, microbial richness is overall higher in lean vs. obese subjects who have lower *Bacteroidetes* to *Firmicutes* ratio, and this correlates with a healthier metabolic profile.

One of the underlying pathogenic characteristics of obesity and T2DM is the presence of low grade systemic inflammation. When the adipose tissue becomes hypertrophic, it secretes pro-inflammatory factors (adipokines) that cause leucocyte infiltration, in turn releasing cytokines that induce insulin resistance and consequently hyperglycaemia, i.e. T2DM. Long-term hyperglycaemia "exhausts" the insulin-producing beta cells, eventually resulting in reducing endogenous insulin production. The negative effects on long-term hyperglycaemia are sometimes termed glucotoxicity and act in concert with lipotoxicity, i.e. negative influences on the pancreatic beta cells from increased blood levels of free fatty acids.

While the adipose tissue has been discussed at great extend as a major source for inflammation the intestinal microbiota is just now emerging as another contributor to systemic inflammation. One hypothesis linking obesity and insulin resistance to changes in the intestinal microbiota is the "leaky epithelium hypothesis", where dysbiosis induced by a fatty "western diet" results in higher intestinal permeability, allowing bacterial endotoxins to enter the circulation. These endotoxins such as lipopolysaccharides (LPS) in turn trigger low-grade inflammation leading to insulin resistance (IR) and, consequently, hyperglycaemia.

Therefore, dietary factors promote low-grade inflammation indirectly through modifications of the intestinal microbiota. Indeed, the "western diet" has notoriously low plant-derived fiber content and is associated with reduced intestinal microbial diversity as compared to diets high in fiber. It has been reported that dietary fibers are fermented by commensal microbes to SCFA such as acetate, propionate and butyrate, that serve as energy sources for colonocytes, regulate intestinal pH levels and affect the host's energy metabolism. Specifically, butyrate has been shown to regulate human dendritic cell maturation and inhibit adipocyte-macrophage inflammatory interactions, while propionate reduces adipokine production in adipose tissue. A reduction in fiber content may therefore result in lower microbial diversity and lower levels of beneficial microbial metabolites, including SCFAs and secondary bile acids. Thereby lack of fiber may contribute to the low-grade systemic inflammation typical for obese and/or T2DM patients.

Since it is known that the IM plays an important role in human health and disease, manipulation of these microorganisms by probiotics, prebiotics and synbiotics are attractive approaches to improve and maintain health. According to the definition formulated by the World Health Organization (WHO) probiotics are "living microorganisms which, when administered in adequate amounts, confer a health benefit on the host. Moreover, prebiotics are used to manipulate the microbiota composition in the GI tract. The definition of prebiotics is even more generic than the one of probiotics: "non-digestible food ingredients that, when consumed in sufficient amounts, selectively stimulate the growth and/or activity(ies) of one or a limited number of microbial genus(era)/species in the gut microbiota that confer(s) health benefits to the host".

Mixture of both probiotics and prebiotics are referred to as synbiotics.

Numerous health-beneficial effects have been attributed to probiotic microorganisms. In general, these health benefits can be categorized into three levels of probiotic action. First of all, probiotic microorganisms can act directly with the GI tract (level 1), for example by direct interaction with the IM or by enzymatic activities. Secondly, they can interact directly with the intestinal mucus layer and epithelium (level 2), thereby influencing the intestinal barrier function and the mucosal immune system. Thirdly, probiotics can have effects outside the GI tract (level 3), for example on the systemic immune system and other organs, such as liver and brain. In general, the mechanism of action of probiotics is quite heterogeneous and depends on the specific strain of microorganism used.

As previously discussed, dysbiosis of the intestinal microbiota has been associated with a growing number of diseases. Since modulation of the composition of intestinal microbiota by probiotics/prebiotics was demonstrated to be possible, probiotic/prebiotic intervention has the potential to counterbalance intestinal dysbiosis and thus restore health. Indeed, probiotic therapy not only introduces bacterial strains with anti-inflammatory properties, but also induces increases of the *Bacteroidetes/Firmicutes* ratio and of specific beneficial strains as demonstrated in animal and human studies. Importantly, successful improvement of the microbiota through probiotics/prebiotics has shown promising outcome in the prevention and treatment of obesity and related diseases, even without modulation of caloric intake. For example, probiotic treatment resulted in reduced blood glucose and haemoglobin A1c levels in patients with T2DM, and may have anti-diabetic effects in protecting pancreatic beta cells from damage. Furthermore, studies on healthy and obese individuals demonstrate expansion in beneficial bacteria of IM such as *Bifidobacterium* species and *Faecalibacterium prausnitzii* during prebiotic treatment. Moreover, administration of the prebiotic oligofructose in obese mice regulates appetite, reduces obesity, and related metabolic disorders. These improvements are associated with 100-fold increase in the abundance of *Akkermansia muciniphila*, increased growth of *Bifidobacteria* and *Lactobacilli*, and expression of antimicrobical peptides by the host. As there is growing evidence that dysbiosis of the intestinal microbiota is associated with the pathogenesis of both intestinal and extra-intestinal disorders, such as inflammatory bowel disease, irritable bowel syndrome (IBS), and coeliac disease, allergy, asthma, metabolic syndrome, cardiovascular disease, and obesity, it is an object of the present invention to provide a product which is able to overcome the drawbacks of the known treatments and at the same time increasing the efficacy of the therapies directed to the treatment of dysbiosis of the intestinal microbiota.

SUMMARY OF THE INVENTION

The above object has been achieved by a pharmaceutical unitary dose comprising at least a probiotic and at least a carotene, as claimed in claim 1.

In a further aspect, the present invention concerns the use of the pharmaceutical unitary dose for the treatment of dysbiosis of the intestinal microbiota, and pathologies ascribable thereto, wherein said at least a probiotic in the presence of at least a carotene produces a therapeutically effective amount of abscisic acid.

In another aspect, the present invention concerns a pharmaceutical composition comprising at least a probiotic, at least a carotene, and at least a xanthophyll.

In a further aspect, the present invention concerns the use of the pharmaceutical composition for the treatment of dysbiosis of the intestinal microbiota, and pathologies ascribable thereto, wherein said at least a probiotic in the presence of at least a carotene produces a therapeutically effective amount of abscisic acid.

In an additional aspect, the present invention concerns a food supplement comprising the pharmaceutical unitary dose or the pharmaceutical composition, and suitable food ingredients.

In a further aspect, the present invention concerns a kit comprising:
i) a first formulation comprising at least a probiotic, and one or more pharmaceutically acceptable excipients;
ii) a second formulation comprising at least a carotene, and one or more pharmaceutically acceptable excipients, and optionally at least a xanthophyll,
iii) a leaflet comprising instructions for using the kit,
for simultaneous, separate or sequential use in the treatment of dysbiosis of the intestinal microbiota, and pathologies ascribable thereto, wherein said at least a probiotic in the presence of at least a carotene produces a therapeutically effective amount of abscisic acid.

In another aspect, the present invention concerns a probiotic for the endogenous production of abscisic acid in the presence of a carotene, for use in the treatment of dysbiosis of the intestinal microbiota, and pathologies ascribable thereto.

In a further aspect, the present invention concerns abscisic acid obtained by a probiotic in the presence of a carotene, for use in the treatment of dysbiosis of the intestinal microbiota, and pathologies ascribable thereto.

BRIEF DESCRIPTION OF THE FIGURES

The characteristics and the advantages of the present invention will become apparent from the following detailed description, the working examples provided for illustrative purposes and the accompanying figures, wherein.

DETAILED DESCRIPTION OF THE INVENTION

Figure 1A:
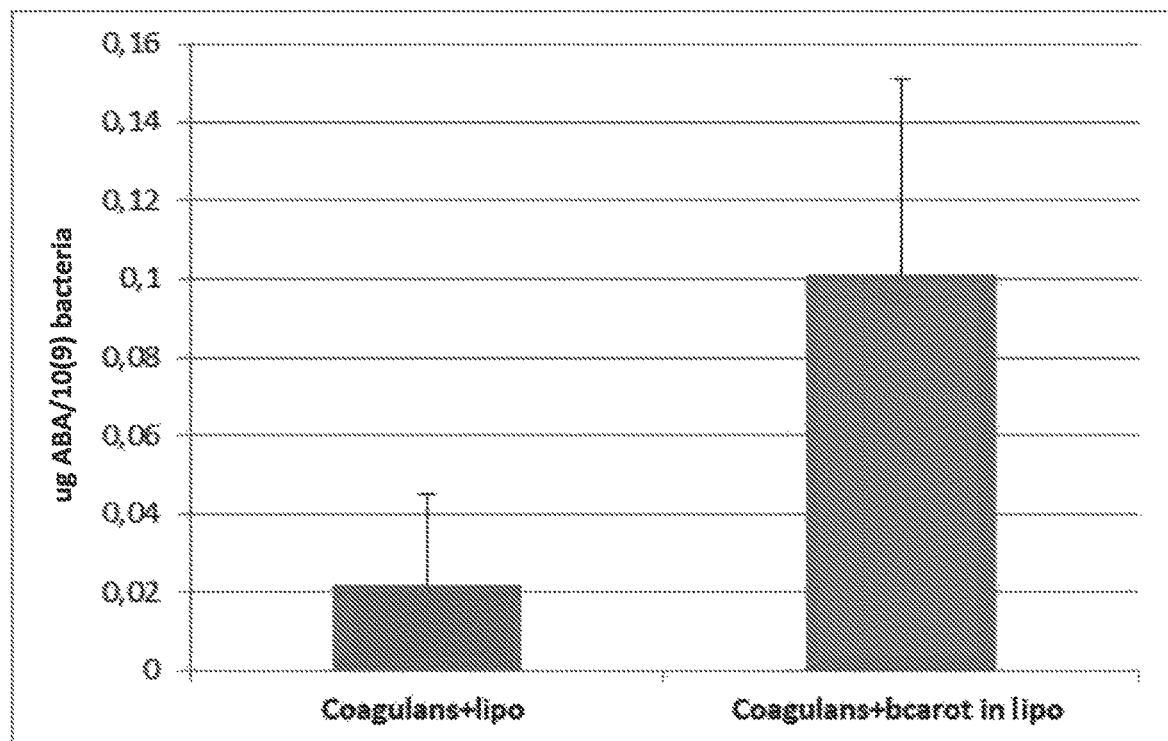
FIG. 1 shows the results of the probiotic incubation with beta-carotene, in terms of abscisic acid production, as per Example 1.

The subject of the invention therefore is a pharmaceutical unitary dose comprising at least a probiotic and at least a carotene, wherein said at least a probiotic is in an amount of at least $1\times10^8$CFU and said at least a carotene is in an amount not higher than 30 mg.

Preferably, said pharmaceutical unitary dose is a pharmaceutical daily unitary dose.

For the purposes of the present invention, said at least a probiotic is a microorganism belonging to the species *Bacillus Coagulans, Bacillus Clausii, Lactobacillus Reuteri, Lactobacillus Plantarum, Lactobacillus Rhamnosus, Lactobacillus Casei, Bifidobacterium Longum*, or a combination thereof.

Preferably, said at least a probiotic is a microorganism belonging to the species *Bacillus Coagulans, Lactobacillus Plantarum, Lactobacillus Rhamnosus*, or a combination thereof.

Preferably, said at least a probiotic is in an amount of at least $1\times10^9$CFU.

Preferably, said at least a probiotic is in an amount not higher than $5\times10^9$CFU.

More preferably, said at least a probiotic is in an amount of $1.2\times10^9$CFU to $5\times10^9$CFU, more preferably $1.5\times10^9$CFU to $4\times10^9$CFU.

Said at least a carotene is a carotenoid containing no oxygen, being α-carotene, β-carotene, γ-carotene, δ-carotene, ε-carotene, lycopene, lycopersene, phytofluene, hexahydrolycopene, torulene, zeacarotene, or a mixture thereof.

Preferably, said at least a carotene is α-carotene, β-carotene, γ-carotene, δ-carotene, ε-carotene, lycopene, or a mixture thereof.

In preferred embodiment, said at least a carotene is β-carotene.

Preferably, and said at least a carotene is in an amount not higher than 25 mg.

More preferably, said at least a carotene is in an amount not higher than 20 mg, more preferably not higher than 10 mg.

In preferred embodiments, said at least a carotene is in an amount of 3-7 mg.

In preferred embodiments, the pharmaceutical composition comprises liposomes carrying at least a carotene.

Preferably, said liposomes comprise phospholipids selected from natural phospholipids, phosphatidic acid, phosphatidylcholine, phosphatidylglycerol, phosphatidylethanolamine, phosphatidylserine, PEG-phospholipid, or mixtures thereof.

More preferably, said liposomes comprise phospholipids selected from soybean phospholipid, egg phospholipid, sunflower phospholipids, egg phosphatidylcholine, soy phosphatidylcholine, hydrogenated soy phosphatidylcholine, phosphatidylcholine sunflower, sphingomyelin, didecanoyl phosphatidylcholine, dilauroyl phosphatidylcholine, dimyristoyl phosphatidylcholine, dipalmitoyl phosphatidylcholine, distearoyl phosphatidylcholine, dioleyl phosphatidylcholine, palmitoyl-oleyl phosphatidylcholine, dilinoleoyl phosphatidylcholine, dierucoyl phosphatidylcholine, didecanoyl phosphatidylglycerol, dilauroyl phosphatidylglycerol, dimyristoyl phosphatidylglycerol, dipalmitoyl phosphatidylglycerol, distearoyl phosphatidylglycerol, dioleyl phosphatidyl glycerol, palmitoyl-oleyl phosphatidylglycerol, dilinoleoyl phosphatidylglycerol, dierucoyl phosphatidylglycerol, didecanoyl phosphatidylethanol-amine, dilauroyl phosphatidylethanolamine, dimyristoyl phosphatidylethanolamine, dipalmitoyl phosphatidylethanolamine, distearoyl phosphatidylethanolamine, dioleyl phosphatidylethanolamine, palmitoyl-oleyl phosphatidylethanolamine, dilinoleoyl phosphatidylethanolamine, dierucoyl phosphatidylethanolamine, dilauroyl phosphatidyl-serine, dimyristoyl phosphatidylserine, dipalmitoyl phosphatidylserine, distearoyl phosphatidylserine, dioleyl phosphatidylserine, dilinoleoyl phosphatidylserine, or a mixture thereof.

In preferred embodiments, said liposomes comprise lecithin, which is a mixture of glycerophospholipids including phosphatidylcholine, phosphatidylethanolamine, phosphatidylinositol, and phosphatidic acid.

Preferably, said at least a probiotic is in an amount of $1\times10^8$CFU to $5\times10^9$CFU and said at least a carotene is in an amount not higher than 25 mg.

Preferably, said at least a probiotic is in an amount of at least $1\times10^9$CFU and said at least a carotene is in an amount not higher than 25 mg, more preferably said at least a probiotic is in an amount of $1.2\times10^9$CFU to $5\times10^9$CFU and said at least a carotene is in an amount not higher than 20 mg.

In particularly preferred embodiments, the pharmaceutical unitary dose comprises at least a probiotic belonging to the species *Bacillus Coagulans, Lactobacillus Plantarum, Lactobacillus Rhamnosus*, or a combination thereof, in an amount of $1\times10^8$CFU to $5\times10^9$CFU and β-carotene in an amount not higher than 10 mg.

In a particularly preferred embodiment, the pharmaceutical unitary dose comprises at least a probiotic belonging to the species *Bacillus Coagulans, Lactobacillus Plantarum, Lactobacillus Rhamnosus*, or a combination thereof, in an amount of $1.2\times10^9$CFU to $2\times10^9$CFU and β-carotene in an amount of 3-7 mg.

In a further aspect, the present invention concerns the use of the pharmaceutical unitary dose for the treatment of dysbiosis of the intestinal microbiota, and pathologies ascribable thereto, wherein said at least a probiotic in the presence of at least a carotene produces a therapeutically effective amount of abscisic acid.

As it will be demonstrated in the following Examples, firstly, it has been surprisingly found that the probiotic of the invention is able to produce abscisic acid (ABA), which, as explained above, improves the metabolic parameters that are altered under conditions of dysbiosis and pathologies ascribable thereto. In this regard, the present invention also concerns a probiotic for the endogenous production of abscisic acid for use in the treatment of dysbiosis of the intestinal microbiota, and pathologies ascribable thereto.

Secondly, it was unexpectedly found that a probiotic in the presence of a carotene and at the indicated amounts, produces abscisic acid at significantly higher levels than those observed for the probiotic alone at the same conditions. The results reported below clearly show that an unexpected synergistic effect is obtained.

It is known that high concentrations of glucose stimulate β-pancreatic cells to release abscisic acid, which in turn induces the release of insulin from the same. In addition, the plasma concentration of abscisic acid is increased in humans after a surfeit of glucose, indicating that abscisic acid is in effect an endogenous human hormone. It has been experimentally demonstrated that, even at extremely low doses, abscisic acid has an ameliorating effect on glycaemic control without however increasing insulin secretion and therefore without representing a potential harm to the population of pancreatic beta-cells, in contrast to current therapeutic strategies.

The effect observed by the above-described pharmaceutical unitary dose is particularly advantageous, since it allows the disadvantages of the prior art to be solved, including those related to conventional hypoglycaemic therapies, which cause an undesired increase in insulin secretion. This effect is also unexpected, given that abscisic acid induces β-pancreatic cells in vitro to release insulin after administration of high concentrations of glucose.

As discussed in the State of the Art, perturbation of the gut microbiota composition results in higher intestinal permeability, allowing bacterial endotoxins to enter the bloodstream; this triggers a systemic low-grade inflammation, which in turn leads to insulin-resistance, hyperglycemia, dyslipidemia and concurs to body fat accumulation (obesity). The results reported in the Examples below indicate that the daily intake of above-described pharmaceutical unitary dose significantly ameliorates most of the metabolic markers altered in a condition of dysbiosis and causing T2D and metabolic syndrome. In particular, the significant reduction of the hs-CRP, a marker of low-grade systemic inflammation, suggests a beneficial action of the probiotic combined with a carotene in lowering gut permeability. As a consequence, a significant improvement of total cholesterol, HDL, LDL, TG, BMI and waist circumference are observed. Moreover, the production of abscisic acid by the probiotic combined with a carotene allows the autocrine stimulation of the probiotic proliferation, thus contributing to its colonization of the gut. The production of abscisic acid by the probiotic combined with a carotene also allows the already reported beneficial systemic effect of abscisic acid on glycemia regulation. Indeed, intake of the probiotic combined with a carotene increases basal plasma ABA 2.3-fold in all subjects, thus reaching concentrations in the range of activity having beneficial effects on hyperglycemia.

Among the pathologies ascribable to dysbiosis of the intestinal microbiota, the following can be mentioned: insulin-resistance, inflammatory bowel disease, irritable bowel syndrome (IBS), and coeliac disease, allergy, asthma, non-insulin-dependent diabetes (NIDDM), syndrome X, obesity, polycystic ovarian disorder (PCOS), hair-AN syndrome, AIDS wasting, intra-uterine growth failure, post-natal growth failure, Prader-Willi syndrome, type 2 diabetes, diabetic complications, hyperglycaemia, dyslipidaemia, metabolic syndrome, hypertension, cardiovascular disease.

In a further aspect, the present invention concerns abscisic acid for use in the treatment of dysbiosis of the intestinal microbiota, and pathologies ascribable thereto.

In another aspect, the present invention concerns a pharmaceutical composition comprising at least a probiotic, at least a carotene, and at least a xanthophyll.

Said at least a xanthophyll is a carotenoid containing oxygen.

A xanthophyll can be alloxanthin, cynthiaxanthin, pectenoxanthin, β-cryptoxanthin, cryptomonaxanthin, crustaxanthin, gazaniaxanthin, HO-chlorobactene, loroxanthin, lutein, lycoxanthin, rhodopin, rhodopinol, saproxanthin, zeaxanthin, oscillaxanthin, phleixanthophyll, rhodovibrin, spheroidene, diadinoxanthin, luteoxanthin, mutatoxanthin, citroxanthin, zeaxanthin furanoxide, violaxanthin, neochrome, foliachrome, trollichrome, vaucheriaxanthin, rhodopinal, warmingone, torularhodinaldehyde, torularhodin, torularhodin methyl ester, astacene, astaxanthin, canthaxanthin, capsanthin, capsorubin, cryptocapsin, 2,2'-diketospirilloxanthin, echinenone, 3'-hydroxyechinenone, flexixanthin, 3-HO-canthaxanthin, hydroxyspheriodenone, okenone, pectenolone, phoeniconone, phoenicopterone, rubixanthone, siphonaxanthin, astacein, fucoxanthin, isofucoxanthin, physalien, siphonein, β-apo-2'-carotenal, apo-2-lycopenal, apo-6'-lycopenal, azafrinaldehyde, bixin, citranaxanthin, crocetin, crocetinsemialdehyde, crocin, hopkinsiaxanthin, methyl apo-6'-lycopenoate, paracentrone, sintaxanthin, actinioerythrin, β-carotenone, peridinin, pyrrhoxanthininol, semi-α-carotenone, semi-β-carotenone, triphasiaxanthin, eschscholtzxanthin, eschscholtzxanthone, rhodoxanthin, tangeraxanthin, nonaprenoxanthin, decaprenoxanthin, bacterioruberin or a mixture thereof.

Preferably, said at least a xanthophyll is alloxanthin, cynthiaxanthin, pectenoxanthin, β-cryptoxanthin, cryptomonaxanthin, crustaxanthin, gazaniaxanthin, HO-chlorobactene, loroxanthin, lutein, lycoxanthin, rhodopin, rhodopinol, saproxanthin, astaxanthin, zeaxanthin, violaxanthin, or a mixture thereof.

More preferably, said at least a xanthophyll is astaxanthin, lutein, zeaxanthin, violaxanthin, or a mixture thereof.

Preferably, said at least a xanthophyll is in an amount not higher than 1 mg.

In preferred embodiments, said at least a xanthophyll is in an amount of 0.05-0.5 mg.

In more preferred embodiments, said at least a xanthophyll is in an amount of about 0.1 mg.

In preferred embodiments, the pharmaceutical composition comprises liposomes carrying at least a carotene, at least a xanthophyll, or a combination thereof.

In a further aspect, the present invention concerns the use of the pharmaceutical composition for the treatment of dysbiosis of the intestinal microbiota, and pathologies ascribable thereto, wherein said at least a probiotic in the presence of at least a carotene produces a therapeutically effective amount of abscisic acid.

As it will be clear from the working Examples given below, it was observed that the presence of a xanthophyll alone significantly reduces the production of abscisic acid by the probiotic. Conversely and unexpectedly, when the probiotic is in the presence of at least a carotene and at least a xanthophyll, the production of abscisic acid by the probiotic is drastically increased. The results reported below clearly show that an unexpected synergistic effect is obtained.

In an additional aspect, the present invention concerns a food supplement comprising the pharmaceutical unitary dose or the pharmaceutical composition, and suitable food ingredients.

The pharmaceutical unitary dose of the invention, as well as the pharmaceutical composition and the food supplement, may further comprise pharmaceutically acceptable excipients. By "excipient" it is meant a compound or a mixture thereof suitable for the use in a pharmaceutical or food formulation. For example, an excipient for use in a pharmaceutical formulation generally should not cause an adverse reaction in a subject, nor it should significantly inhibit the efficacy of the active principles.

Suitable excipients are acidifying agents, acidity correctors, anti-agglomerants, antioxidants, fillers, resistance agents, gelling agents, coating agents, modified starches, sequestering agents, thickeners, sweeteners, thinners, solvents, disaggregating agents, glidants, dyes, binders, lubricants, stabilizers, adsorbents, preservatives, wetting agents, flavors, film-forming substances, emulsifiers, wetting agents, release retardants and mixtures thereof.

Preferably, said excipients are starch, modified starch, cellulose, modified cellulose, microcrystalline cellulose, sodium carboxymethylcellulose, pectin, tragacanth, mannitol, dicalcium phosphate, xanthan gum, carrageenan, sodium alginate, guar gum, maltodextrin, silicon dioxide, or mixtures thereof.

The composition of the present invention can be prepared by methods known in the art. In fact, for oral administration, the components may, for example, be mixed with one or more excipients, enclosed in a soft gel capsule, capsule, tablet, mini-tablet, micro-tablet, granule, micro-granule, pellets, multiparticulate, micronized particulate, powder, solution, suspension, dispersion, emulsion, gel, drop, or aerosol, preferably capsule.

In a further aspect, the present invention concerns a kit comprising:
 i) a first formulation comprising at least a probiotic, and one or more pharmaceutically acceptable excipients;
 ii) a second formulation comprising at least a carotene, and one or more pharmaceutically acceptable excipients, and optionally at least a xanthophyll,
 iii) a leaflet comprising instructions for using the kit, for simultaneous, separate or sequential use in the treatment of dysbiosis of the intestinal microbiota, and pathologies ascribable thereto, wherein said at least a probiotic in the presence of at least a carotene produces a therapeutically effective amount of abscisic acid.

The pharmaceutical unitary dose of the invention, as well as the pharmaceutical composition, the food supplement and the kit, may be administered via oral, sublingual, or buccal route, preferably, via oral route.

It should be understood that all the aspects identified as preferred and advantageous for the pharmaceutical unitary dose are to be deemed as similarly preferred and advantageous also for the pharmaceutical composition, the food supplement, the kit, and uses of the same.

It should be also understood that all the combinations of preferred aspects of the pharmaceutical unitary dose of the invention, as well as of the pharmaceutical composition, the food supplement, the kit and uses of the same, as above reported, are to be deemed as hereby disclosed.

Below are working examples of the present invention provided for illustrative purposes.

EXAMPLES

Materials

*Bacillus coagulans* was from ATCC (Virginia, USA) and from tablets commercially available (Thorne Research, Dover, UK). The mixture of *Lactobacillus plantarum* and *Bacillus coagulans* was from ProLife, a commercially available product of Zeta Farmaceutici (Sandrigo, Vicenza, Italy); *Lactobacillus rhamnousus* was from Kaleidon 60, a commercially available product of Malesci (Grassina, Firenze, Italy). Beta-carotene and LB medium were purchased from Sigma (Milano, Italy); zeaxanthin was obtained from BioReagents (Montigny, France). Abscisic acid ELISA Kit was purchased from Agdia Biofords (Evry Cedex, France).

Example 1

Bacterial Cell Culture

Lyophilized probiotics were grown separately in LB medium in shake-flasks equipped with vented cap at 37° C. for 24 hours. After growth, each probiotic suspension was diluted with LB medium to reach approximately 0.1 O.D. at 600 nm. 3.5 ml of each diluted suspension was added with 500 µl of:
 i) empty liposomes,
 ii) liposomes containing 1 mg carotene,
 iii) liposomes containing 0.1 mg xanthophyll,
 iv) both liposomes containing carotene and xanthophyll, and
 incubated with shaking at 350 rpm at 37° C. for 24 hours.

At the end of the incubation, each probiotic suspension was pelleted by centrifugation at 3000×g for 10 minutes. Supernatant was recovered, added with 4 vol of methanol and stored at −20° C. for 24 hours. Pellet was washed once with saline buffer, centrifuged at 3000×g for 10 minutes, resuspended in 2 ml of methanol, sonicated in ice and stored at −20° C. for 24 hours.

Liposomes Preparation 4 mg of carotene and 0.4 mg of xanthophyll were dissolved each in 200 µl of chloroform by vortexing. For each liposome preparation 200 mg of lecithin were dissolved in 500 µl of chloroform. Both carotene and xanthophyll chloroform solutions were added, separately, to the chloroform lecithin solution, vortexed, and completely dried with $N_2$ to create a thin layer on the inner wall of a glass Corex. The thin layer was detached with 2 ml of LB medium by vortexing at maximum speed and the solution obtained was finally sonicated on ice to obtain liposomes. The final concentration of carotene and xanthophyll in 500 µl of each liposome preparation used for bacteria incubation was 1 mg and 0.1 mg, respectively.

To prepare empty liposomes or liposomes with carotene or liposomes with xanthophyll, were added to the chloroform lecithin solution the same volume of chloroform, i.e. 200 µl, used to dissolve carotene and xanthophyll.

Detection of Abscisic Acid Produced by Bacteria

Quantification of abscisic acid (ABA) was performed on both pellets and supernatants obtained as described above (see Bacterial cell culture). Briefly, after 24 hours at −20° C. in methanol, pellets and supernatants were centrifuged at 3000×g for 5 minutes. Supernatant from each centrifuged sample was recovered, lyophilized, resuspended in 500 µl of TRIS buffer provided by the ABA ELISA kit and filtered with spin-x in microfuge for 30 min at maximum speed. Measurement of ABA was performed in quadruplicate on each sample according to manufacturer's instructions of the ELISA kit.

Result Discussion

In FIG. 1A, it was reported the comparison between a culture of *Bacillus coagulans* and empty liposomes, and a culture of *Bacillus coagulans* and liposomes containing 1 mg beta-carotene. It is clearly shown that, in the presence of beta-carotene, the production of abscisic acid is drastically increased, i.e. about 6.6 times higher (p=0.0093).

The abscisic acid produced corresponds to 0.1 µg/10(9) bacteria. Considering the bacterial intestinal content (in the colon) of 10(12) bacteria/g, the amount of abscisic acid produced in vivo, if all the bacteria per g of the intestine were *Bacillus coagulans*, would have been 100 ug/10(12) bacteria/g. In other words, 50 ug abscisic acid per 0.5 g of intestinal contents. Hypothetically supposing that *Bacillus coagulans* content of 1/100 of bacteria/g of intestinal contents, 50 g of that intestinal content would be sufficient to reach the amount of abscisic acid needed.

Figure 1B:
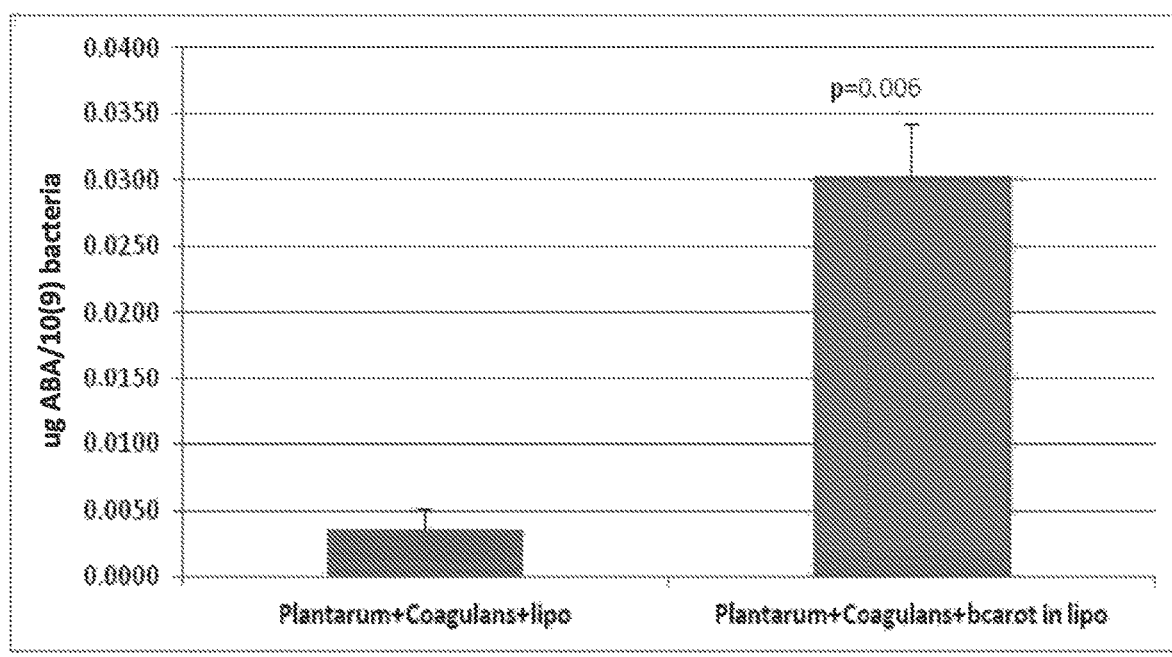

In FIG. 1B, it was reported the comparison between a culture of *Bacillus coagulans*, *Lactobacillus Plantarum* and empty liposomes, and a culture of *Bacillus coagulans*, *Lactobacillus Plantarum* and liposomes containing 1 mg beta-carotene. It is clearly shown that, in the presence of beta-carotene, the production of abscisic acid is drastically increased, i.e. about 7.5 times higher.

Figure 1C:
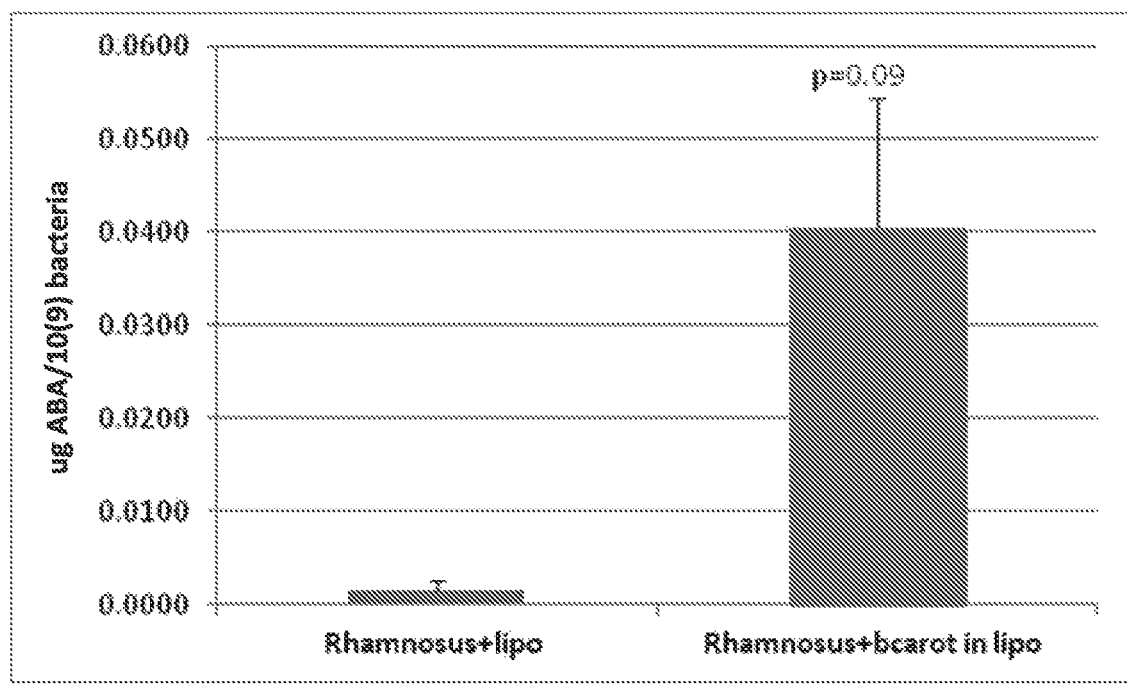

In FIG. 1C, it was reported the comparison between a culture of *Lactobacillus Rhamnosus* and empty liposomes, and a culture of *Lactobacillus Rhamnosus* and liposomes containing 1 mg beta-carotene. It is clearly shown that, in the presence of beta-carotene, the production of abscisic acid is drastically increased, i.e. about 20 times higher.

Figure 2:
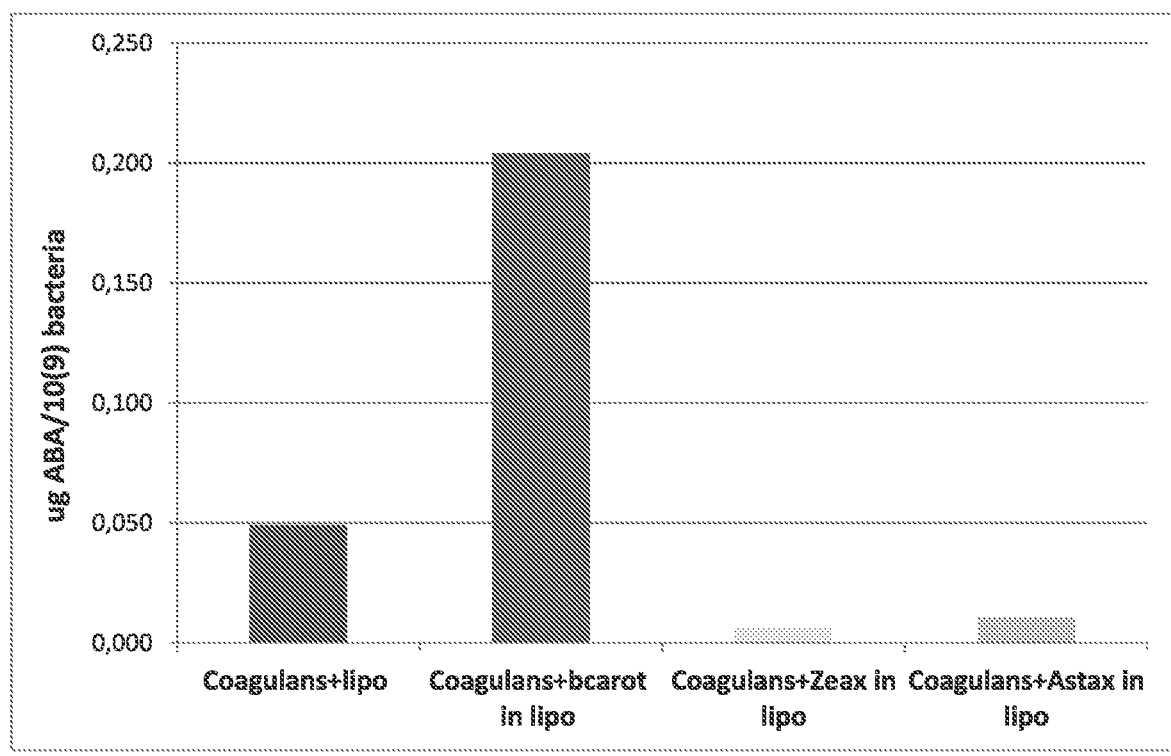
FIG. 2 shows the results of the probiotic incubation with different carotenoids, in terms of abscisic acid production, as per Example 1.

In FIG. 2, it was reported the comparison between:
a culture of *Bacillus coagulans* and empty liposomes,
a culture of *Bacillus coagulans* and liposomes containing 1 mg beta-carotene,
a culture of *Bacillus coagulans* and liposomes containing 0.1 mg zeaxanthin,
a culture of *Bacillus coagulans* and liposomes containing 0.1 mg astaxanthin, It is clearly shown that, in the presence of beta-carotene, the production of abscisic acid is drastically increased, i.e. about 5 times higher, whereas in the presence of a xanthophyll, the production of abscisic acid is unexpectedly and significantly reduced.

Figure 3:
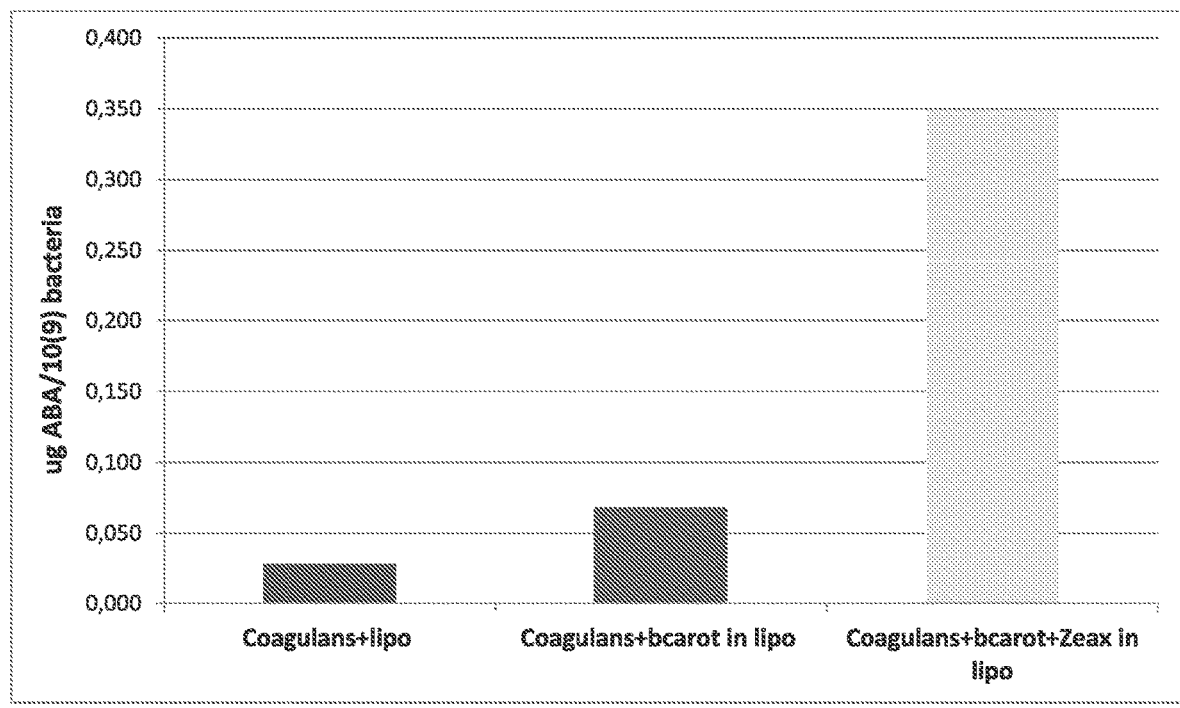
FIG. 3 shows the results of the probiotic incubation with a carotene and a xanthophyll, in terms of abscisic acid production, as per Example 1.

In FIG. 3, it was reported the comparison between:
a culture of *Bacillus coagulans* and empty liposomes,
a culture of *Bacillus coagulans* and liposomes containing 1 mg beta-carotene,
a culture of *Bacillus coagulans* and liposomes containing 1 mg beta-carotene and 0.1 mg zeaxanthin.

It is clearly shown that, in the presence of beta-carotene and zeaxanthin, the production of abscisic acid is drastically increased, i.e. 10 times higher when compared to the culture of *Bacillus coagulans* alone, and 5 times higher when compared to the culture of *Bacillus coagulans* in the presence of beta-carotene alone.

These results were absolutely unexpected and significant, especially in view of the fact that a xanthophyll, when present alone, reduces the production of abscisic acid of the probiotic, whereas in the concomitant presence of a carotene, a synergistic effect is clearly observed.

Detection of ABA in Human Plasma

Human blood samples (5 ml), drawn in heparin, were centrifuged immediately after withdrawal at 2000×g for 10 minutes. Two milliliters of plasma were immediately extracted with 4 vol methanol, stored at −20° C. for 24 hours and after centrifuged at 3000×g for 5 minutes. Supernatant was recovered, lyophilized, resuspended in 250 µl of TRIS buffer provided by the ABA ELISA kit and filtered with spin-x in microfuge for 30 min at maximum speed. Measurement of ABA was performed in quadruplicate on each sample according to manufacturer's instructions of the ELISA kit.

Human Volunteers

Four healthy volunteers were instructed not to change their dietary habits during the period of the study, and to take one tablet of *Bacillus coagulans* containing $2 \times 10^9$ CFU (Thorne Research, Dover, UK) and one tablet containing 7 mg of beta-carotene (Natural Point, Milano, Italy) daily, before breakfast. At the beginning of the study (day 1) and after 15 days of treatment (day 15), a blood sample was taken from each subject, after overnight fasting, and waist circumference and BMI were measured. Measurement of fasting glycemia (FBG), total, LDL and HDL cholesterol, triglycerides was performed by the clinical chemistry laboratory of the IRCCS Polyclinic Hospital San Martino-IST in Genova. Measurement of hs-CRP was performed by using a specific ELISA kit (Cayman Chemical, Michigan, USA) according to manufacturer's instructions.

In Table 1 below, the mean values of the metabolic parameters of four subjects treated for 15 days with *Bacillus coagulans* and beta-carotene, are reported.

TABLE 1

| Metabolic markers | day 1 | day 15 | P value |
|---|---|---|---|
| Cholesterol | 196 ± 17 | 180 ± 18 | p = 0.07 |
| HDL | 65 ± 15 | 78 ± 16 | p = 0.0002 |
| LDL | 109 ± 11 | 90 ± 16 | p = 0.053 |
| TG | 111 ± 14 | 74 ± 23 | p = 0.044 |
| Cardiovascular risk | 3.1 ± 0.7 | 2.4 ± 0.5 | p = 0.019 |
| Cardiovascular protection | 3.2 ± 0.05 | 4.3 ± 0.06 | p = 0.004 |
| hs-CRP | 4.29 ± 1.19 | 3.64 ± 1.20 | p = 0.005 |
| BMI | 22.9 ± 4.6 | 22.5 ± 4.7 | p = 0.0023 |
| Waist circumference (cm) | 78.8 ± 3.6 | 78.0 ± 3.4 | p = 0.019 |

As reported in the State of the Art, perturbation of the gut microbiota composition results in higher intestinal permeability, allowing bacterial endotoxins to enter the bloodstream; this triggers a systemic low-grade inflammation, which in turn leads to insulin-resistance, hyperglycemia, dyslipidemia and concurs to body fat accumulation (obesity). The results summarized in Table 1 indicate that the daily intake of a probiotic and carotene significantly ameliorates most of the metabolic markers altered in a condition of dysbiosis and causing T2D and metabolic syndrome. In particular, the significant reduction of the hs-CRP, a marker of low-grade systemic inflammation, suggests a beneficial action of probiotic combined with a carotene in lowering gut permeability. As a consequence, a significant improvement of total cholesterol, HDL, LDL, TG, BMI and waist circumference are observed in all subjects. Moreover, production of ABA by probiotic combined with a carotene (shown in FIGS. 1A, 2) allows the autocrine stimulation of the probiotic proliferation, contributing to its colonization of the gut. Production of ABA by probiotic combined with a carotene also allows the already reported beneficial systemic effect of ABA on glycemia regulation. Indeed, intake of probiotic combined with a carotene increased basal plasma ABA 2.3-fold in all subjects (FIG. 4), thus reaching concentrations in the range of activity having beneficial effects on hyperglycemia.

Figure 4:
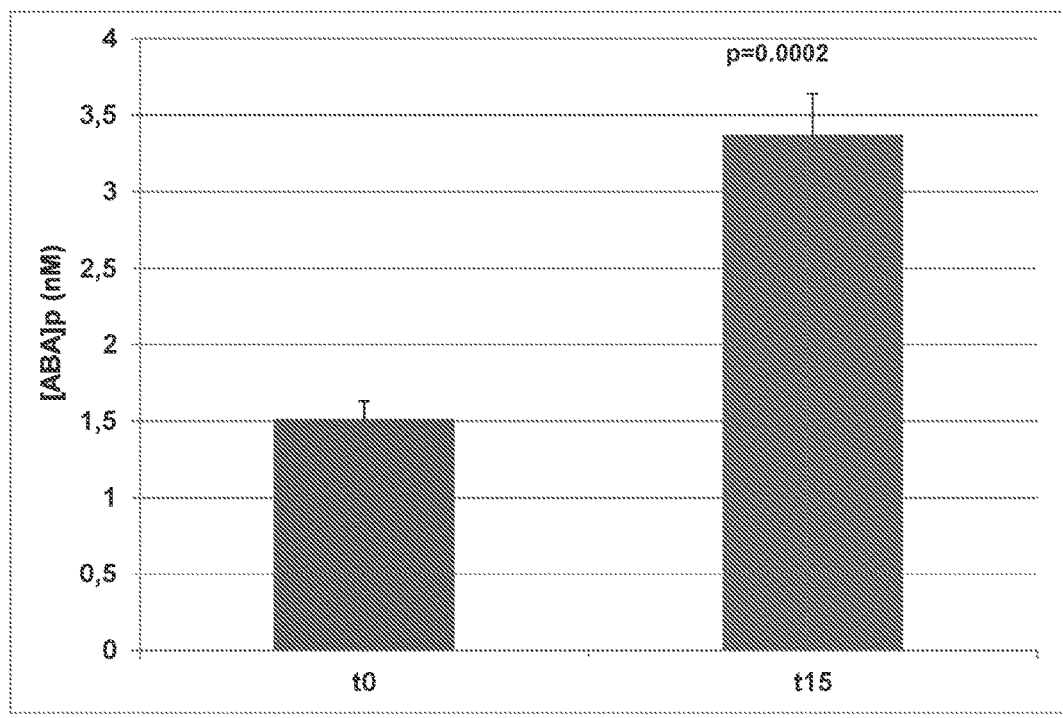
FIG. 4 shows of the in vivo experimentation on healthy volunteers, as per Example 1.

In FIG. 4, it was reported the comparison between the plasma concentration of abscisic acid at the beginning of the study (t0) and after 15 days (t15). The plasma concentration increases on average and significantly by 2.3 times reaching a stable and effective value of 3.4 nM (corresponding to 4.45 µg in the blood stream).

The invention claimed is:

1. A pharmaceutical daily unitary dose for treating dysbiosis of intestinal microbiota, said pharmaceutical unitary dose comprising at least a probiotic and at least a carotene, wherein said at least a probiotic is a microorganism belonging to the species *Bacillus coagulans, Bacillus clausii, Lactobacillus reuteri, Lactobacillus plantarum, Lactobacillus rhamnosus, Lactobacillus casei, Bifidobacterium longum*, or a combination thereof in an amount of at least $1\times10^8$CFU and not higher than $5\times10^9$CFU and said at least a carotene is in an amount of from 1 mg to no more than 30 mg.

2. The pharmaceutical unitary dose of claim 1, wherein said at least a probiotic is a microorganism belonging to the species *Bacillus Coagulans, Lactobacillus Plantarum, Lactobacillus Rhamnosus*, or a combination thereof.

3. The pharmaceutical unitary dose of claim 1, wherein said at least a probiotic is in an amount of at least $1\times10^9$CFU.

4. The pharmaceutical unitary dose of claim 1, wherein said at least a probiotic is in an amount of $1.2\times10^9$CFU to $5\times10^9$CFU.

5. The pharmaceutical unitary dose of claim 1, wherein said at least a carotene is α-carotene, β-carotene, γ-carotene, δ-carotene, ε-carotene, lycopene, or a mixture thereof.

6. The pharmaceutical unitary dose of claim 1, wherein said at least a carotene is in an amount of from 1 mg to no more than 25 mg.

7. The pharmaceutical unitary dose of claim 1, wherein said at least a probiotic is in an amount of $1.5\times10^9$CFU to $4\times10^9$CFU and said at least a carotene is in an amount of from 1 mg to no more than 20 mg.

8. The pharmaceutical unitary dose of claim 1 further comprising at least a xanthophyll in an amount of from 0.1 mg to 1 mg.

9. The pharmaceutical composition of claim 8, wherein said at least a xanthophyll is astaxanthin, lutein, zeaxanthin, violaxanthin or a mixture thereof.

10. The pharmaceutical unitary dose of claim 1, wherein said at least a carotene is βcarotene.

* * * * *